United States Patent
Van Olmen et al.

(10) Patent No.: US 11,249,030 B2
(45) Date of Patent: Feb. 15, 2022

(54) PRODUCT INSPECTION AND CHARACTERIZATION DEVICE

(71) Applicant: Multiscan Technologies, S.L., Cocentaina (ES)

(72) Inventors: Simon Hendrik E. Van Olmen, Muro de Alcoy (ES); Álvaro Soler Esteban, Alcoy (ES)

(73) Assignee: Multiscan Technologies, S.L., Cocentaina (ES)

( * ) Notice: Subject to any disclaimer, the term of this patent is extended or adjusted under 35 U.S.C. 154(b) by 0 days.

(21) Appl. No.: 16/756,969

(22) PCT Filed: Nov. 3, 2017

(86) PCT No.: PCT/ES2017/070730
§ 371 (c)(1),
(2) Date: Apr. 17, 2020

(87) PCT Pub. No.: WO2019/086727
PCT Pub. Date: May 9, 2019

(65) Prior Publication Data
US 2021/0223185 A1 Jul. 22, 2021

(51) Int. Cl.
*G01J 3/28* (2006.01)
*G01N 21/89* (2006.01)
(Continued)

(52) U.S. Cl.
CPC ....... *G01N 21/8901* (2013.01); *G01N 21/255* (2013.01); *G01N 33/02* (2013.01); *G01N 2201/06113* (2013.01)

(58) Field of Classification Search
CPC .... G01J 3/02; G01J 3/28; G01J 3/2803; G01J 3/10; G01J 3/2823
(Continued)

(56) References Cited

U.S. PATENT DOCUMENTS

| 5,410,154 A | 4/1995 | Broicher et al. |
| 2002/0041377 A1* | 4/2002 | Hagiwara ............... G03F 7/707 356/399 |

(Continued)

FOREIGN PATENT DOCUMENTS

EP 1 197 742 A1 4/2002

OTHER PUBLICATIONS

International Search Report of PCT/ES2017/070730, dated Jun. 26, 2018.

*Primary Examiner* — Md M Rahman
(74) *Attorney, Agent, or Firm* — Collard & Roe, P.C.

(57) ABSTRACT

The invention relates to a product inspection and characterization device, including conveyance means, a two-dimensional inspection region, a radiation source generating a spot light beam for partially illuminating the surface of the product, optical means for directing the light beam provided with at least one mirror to aim the spot light beam in the inspection region, optical means for directing the reflected and/or scattered light to detection means, detection means for analyzing the light scattered and/or reflected by the product and a processing unit for characterizing the product. The radiation source emitting the light beam is therefore pointed at the product by optical means directing the light beam to the two-dimensional inspection region. Another object of the present invention relates to the method for product inspection and characterization.

14 Claims, 3 Drawing Sheets

(51) Int. Cl.
*G01N 21/25* (2006.01)
*G01N 33/02* (2006.01)

(58) Field of Classification Search
USPC .......................................................... 356/326
See application file for complete search history.

(56) References Cited

U.S. PATENT DOCUMENTS

2013/0258332 A1* 10/2013 Iga ........................... G01J 3/26
356/301
2014/0333755 A1  11/2014 Adams et al.
2016/0091434 A1   3/2016 Fagan et al.

* cited by examiner

PRODUCT INSPECTION AND CHARACTERIZATION DEVICE

CROSS REFERENCE TO RELATED APPLICATIONS

This application is the National Stage of PCT/ES2017/070730 filed on Nov. 3, 2017, the disclosure of which is incorporated by reference. The international application under PCT article 21(2) was not published in English.

TECHNICAL FIELD

The present invention relates to a device for inspecting and characterizing a product, preferably food, by analyzing the light reflected and/or scattered by the product, where the device is provided with a spot light source, the beam of which is directed towards the product to be inspected using optical means which make movement of the light beam in two axes possible.

The object of the invention is to provide a device which makes quick product inspection possible since the spot light beam is specifically directed on the inspection region through which the product to be inspected moves, the light beam at least partially illuminating the surface of the product to be inspected.

Another object of the present invention relates to the method that is carried out for product inspection and characterization, where one of its essential steps consists of guiding the spot light beam by means of movement in two axes, making it possible to move the light beam in order to suitably point it at that region where the product is located or region of the product to be inspected.

PRIOR ART

Inspection devices which allow characterizing a food product by means of using a light beam that completely illuminates the product are known. An example of these devices is disclosed in patent document number EP1197742, describing an inspection device for inspecting the internal quality of a product using a type of on-line multiple-lamp. The device is made up of multiple light sources focused on the product for inspection, the device analyzing the light going through the product.

This device has the major drawback of using a high-power lamp for the inspection for the purpose of obtaining a spectrum of the light beam that completely goes through the product. In this sense, the use of a high-power lamp means exposing the product to be inspected to a high temperature, where its organoleptic properties may even be affected. On the other hand, the use of high-power lamps entails a high energy expenditure.

Additionally, devices used in food product inspection applications using a laser in combination with a rotary mirror to make movement of the mentioned laser possible are known. These devices only enable movement in one axis, performing a fixed, single-line scan, and therefore exposing the product to be illuminated to the laser for a very short time.

Even in those known inspection devices in which a laser illuminating the products to be characterized is used, this laser does not move in two dimensions, so the device scans the entire region where the products to be sorted are deposited.

The drawback of these devices resides in the imperative need to generate a scan line that scans the entire surface of the inspection region and must therefore move at a high speed. Therefore, the amount of light scattered and/or reflected by the product to be inspected is very small and the time of analysis of the received signal is very short, which hinders the possibility of performing a spectrometric analysis of the product.

In this sense, the detector that usually complements known devices of this type must analyze the return generated by the light beam that has swept the entire inspection surface. The drawback of this system is that the movement of the light beam must be very fast, so the time of analysis is very short and the amount of light reflected and/or scattered by the product is very small. For this reason, very quick detectors are required in these systems and the use of spectrometric-type detectors is not viable.

In summary, the known product inspection and characterization devices are devices that use high-power lamps to completely illuminate the product, obtaining a single return signal after exposing the product to a high temperature which may have a deleterious effect; or they are devices that include a laser that moves in one axis, generating a continuous scan, i.e., completely sweeping the entire inspection region on which the products to be characterized are deposited, offering a very low return signal and not allowing the use of spectral detectors. Devices including very sensitive and quick detectors, where the signal returned by the devices cannot be used for spectrometric analysis, are also known.

Based on the foregoing, there has not been a known inspection and characterization device which makes movement of a spot light beam in two axes possible, partially illuminating the surface of the product and generating high quality return signals for subsequent spectrometric analysis in the prior art up until now.

DISCLOSURE OF THE INVENTION

The problems described above are solved by means of the inspection and characterization device of the present invention.

The spot light beam that the device contains does not sweep the entire surface where the products are deposited, i.e., it does not generate a continuous sweep or scan line for sweeping the entire inspection region.

To that end, the product inspection and characterization device is provided with:
  product conveyance means,
  a two-dimensional inspection region through which the products are moved by the conveyance means,
  a radiation source generating a spot light beam to at least partially illuminate the surface of the product,
  optical means for directing the light beam, which are provided with at least one mirror to aim the spot light beam in the inspection region,
  optical means for directing the reflected and/or scattered light to detection means,
  detection means for analyzing the light scattered and/or reflected by the product,
  processing unit for characterizing the product.

The presence of at least one mirror which makes directing the spot light beam emitted by the radiation source possible is one of the novel effects generated by the present invention, since the light beam can therefore be pointed at a wide range of directions to direct it to the two-dimensional inspection region. The device of the present invention therefore allows controlling the movement of the emitted beam and only scans the regions of interest of the inspection region, offering localized measurements, so the device allows evaluating a specific area or different points within a two-dimensional area.

The present invention is therefore a faster and more effective inspection and characterization system as it significantly reduces the number of measurements to be analyzed for characterizing the product.

The optical means of the invention can comprise a mirror with movement in two axes, although as will be described in detail below, the preferred embodiment of the invention is provided with optical means comprising two mirrors assembled on two perpendicular axes, where one mirror moves in the X axis and the other mirror moves in the Y axis. The mirrors making up the optical means therefore preferably include a galvanometric drive for moving the mentioned mirrors.

Additionally, means can be incorporated for controlling the movement of the mirrors through a programming machine implementing the desired time sequences for obtaining a longer light beam exposure time at those points of interest where food products to be inspected are located for the purpose of obtaining a greater return signal.

Regarding the conveyance means, it must be indicated that said conveyance means can be made up of a roller conveyor, such that the product to be inspected and characterized rotates about itself while at the same time it moves forward through the inspection region. Advantageously, the presence of rotation means such as roller conveyors allows taking several product measurements, i.e., allows inspecting each product on different sides.

The light beam is therefore made to strike several points of the surface of the same product in order to obtain different measurements to be analyzed which make better characterization of the product possible.

In this sense, it must be highlighted that agricultural products have internal qualities that are different for each of them, such as their sugar content, acidity, degree of ripeness, etc. The mentioned parameters can even vary for each part of the product depending on whether said part has been more or less exposed to the sun. The values obtained when projecting the light of a single lamp on a product can therefore vary greatly depending on the direction of the projected light. This aspect is therefore particularly interesting and advantageous when the product to be analyzed is a food product such as a piece of fruit or vegetables.

The roller conveyor can therefore demarcate a line of individual cradles that are arranged in series and move forward one by one into the inspection device, such that a unit of the product to be inspected and characterized is deposited in each cradle.

Advantageously, the roller conveyor will demarcate several lines of individual cradles, making it possible to substantially increase the production capacity of the device.

Complementarily, the inspection and characterization device of the invention can be provided with a viewing system for detecting the position of the objects to be inspected that are located in the inspection region, and specifically directing the light beam thereon. The spot light will therefore strike the position where the product is located.

Therefore, the spot light beam is of a small size and produces a halo around the beam itself, generated from the light that has penetrated the product and then internally scattered. So, when the light of the mentioned halo is analyzed, the light of the spot beam which has partially gone through the product and scattered inside same is being analyzed. It is known that spectral analysis of the light which has partially or completely gone through a product, allows obtaining information about its chemical composition and intrinsic properties.

In a preferred embodiment, a supercontinuum laser-type light source having the advantage of offering a wide spectrum of illumination, preferably between 400 and 2400 nm, in addition to offering a spatially coherent, i.e., non-diverging light beam will be used.

Advantageously, this type of light beam makes it possible to better focus the light that strikes the product to be inspected. Taking into account that the light beam of the invention moves in two dimensions, it will illuminate products at different focal distances, so the spatially coherent light beam will illuminate a region the surface area of which is almost the same, regardless of whether the product is located at a slightly different distance.

In other solutions in which the analysis is performed by means of light transmission, the amount of light which can go through the samples greatly depends on the size and the opacity of the sample. This drawback is greatly minimized with the solution herein presented as the product analysis is performed without the light having to go through the entire sample.

Methods for measuring the internal quality of agricultural products including a light reflection method and a light transmission method are known. In the light reflection method, information about the internal quality is detected through a reflected light obtained from the agricultural product by projecting light beams including near-infrared rays on the agricultural product. In the light transmission method, information about the internal quality is detected based on the transmission of light projected on the agricultural product, through said product.

Additionally, the optical means directing the reflected and/or scattered light comprise a blocking element to prevent the reflected light from returning to the detection means. The inclusion of the blocking elements allows obtaining a return signal that only includes the halo of light which has partially gone through the product and not that which has been reflected by the central region of incidence, so it allows obtaining data that is more representative of the internal part of the product than in the case of not including the blocking element. By adjusting the size of the blocking element, light which has interacted at a greater depth in the product can be analyzed, where the greater the distance it is from the center, the greater the distance it traveled through the product.

Optionally, the optical means directing the reflected and/or scattered light are means independently collecting the reflected light and the scattered light to send the same to different detection means. This allows analyzing the reflected and scattered light with different equipment in order to perform an independent treatment and to obtain more information about the product that is being inspected. The light reflected in the region of incidence of the light beam provides information about the more superficial characteristics of the product to be inspected, whereas the light that has been scattered provides information about the internal part of the product.

Among the detection means that can be used for analyzing the light scattered and/or reflected by the product, at least one spectrometer can be used. Spectrometric analysis is a technique commonly used for analyzing the internal quality of fruits and vegetables.

Another optional element that can be included in the inspection and characterization device of the invention is the element which includes means for sorting the product. This allows the product to be finally sorted according to the analyzed measurements once it has been inspected and characterized by the processing unit.

The steps making up the method for product inspection and characterization using a device such as the one described in detail above are described below:
- the conveyance means moving the product through the detection region,
- the radiation source emitting a light beam,
- orienting the path of the light beam by means of moving a mirror in one or two dimensions to direct the light beam on the products to be inspected,
- projecting the emitted spot light beam on the product,
- returning of the emitted light that has been reflected and/or scattered by the product,
- measuring the reflected and/or scattered light,
- analyzing the measurement for characterizing the product,
- sorting the product based on the obtained characterization.

As explained above, the device can incorporate a vision system which allows it to establish an additional prior step of detecting the position of the product to be inspected. In this sense, this step is constantly repeated throughout the inspection method.

Additionally, the method for inspection and characterization of the present invention additionally includes a step of filtering certain wavelengths of the reflected and/or scattered light beam in order to analyze only those of interest.

The detection means can consist of any type of light detector, including photodiodes, photomultiplier tubes and spectrometers. The detection means can be combined with filters for selecting spectrum bands, as well as for differentially analyzing both reflected and scattered light ("halo"). All of this is known in the prior art. In the case of performing fluorescence analysis, filters for blocking certain wavelengths of the illumination beam, which coincide with those in which the fluorescence phenomenon occurs, can be used.

The system of the invention is not limited to using only one or two radiation spectral bands. The system of the invention can therefore work with a multiplicity of color bands, since the technique does not impose any restriction on the type of emitted light and detection equipment used.

Finally, it must be pointed out that if the detection means are provided with a spectrometer, the measurement of the reflected and/or scattered light will be a spectral measurement, where very precise measurements for characterizing the product can be provided.

DESCRIPTION OF THE DRAWINGS

To complement the description that will be made below and for the purpose of helping to better understand the features of the invention according to a preferred practical embodiment thereof, a set of drawings is attached as an integral part of said description, in which the following is depicted with an illustrative and non-limiting character.

DETAILED DESCRIPTION OF THE PREFERRED EMBODIMENT

Figure 1:
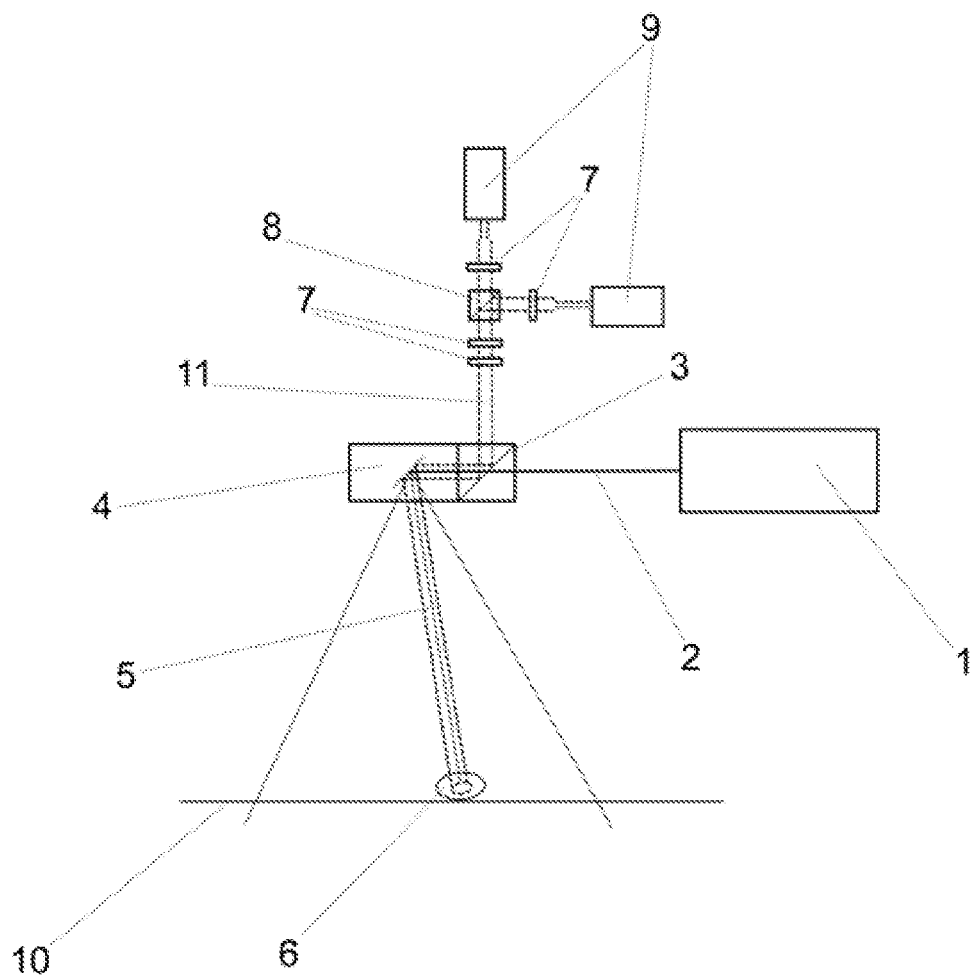
FIG. 1 shows a schematic perspective view of a sorting apparatus as described in the present invention.

FIG. 1 shows a preferred embodiment of the device of the present invention which is provided with the following elements:

1. Light source, preferably a supercontinuum laser, but it may also be any other type of monochrome laser, a combination thereof, an LED light source or any spot light source with collimated beam.
2. Light beam that will be projected on the objects.
3. Mirror. The function of this element is to divert the path of the light which has interacted with the object to the detector elements.
4. Set of galvanometric mirrors. These mirrors allow moving the light beam in one or two dimensions to focus it on the objects to be inspected.
5. Light beam projected on the object and a return trajectory for the light which has interacted with the object.
6. Object to be inspected.
7. Set of optical elements for filtering specific wavelengths, focusing, and/or masking a certain region of the reflected light (for example, the center of the beam which is reflected light, the outermost part of the beam is light which has interacted with the object)
8. Beam splitting element. This element can be a simple beam splitter or will preferably be a mirror that only reflects certain wavelengths of interest, for example, for separating wavelengths of 450~1000 nm to one detector and wavelengths of 1000~2400 nm to another detector.
9. Detector. The detector can be any type of point detector which is sensitive in the range of the spectrum to be analyzed, but will preferably be a spectral detector, which is capable of measuring spectral information of the light striking the detector. It is also possible to use area sensors for analyzing light scattering in the object.
10. Conveyance system moving the products to be analyzed through the inspection region.
11. Return signal The system will preferably be assembled on a conveyor belt, in combination with another conventional vision system, which can obtain information and detect the position of the objects to be inspected. The analysis system will then move the scanning beam on the objects, taking into account the coordinates obtained with the conventional vision system, as well as the forward movement speed of the conveyance system. When taking a measurement of the object, a single localized analysis can be performed or a two-dimensional scanning of the object can also be carried out to obtain an image. A two-axis galvanometer head system is used for this application, obtaining the signal from the detectors when the beam strikes the objects.

Figure 2:
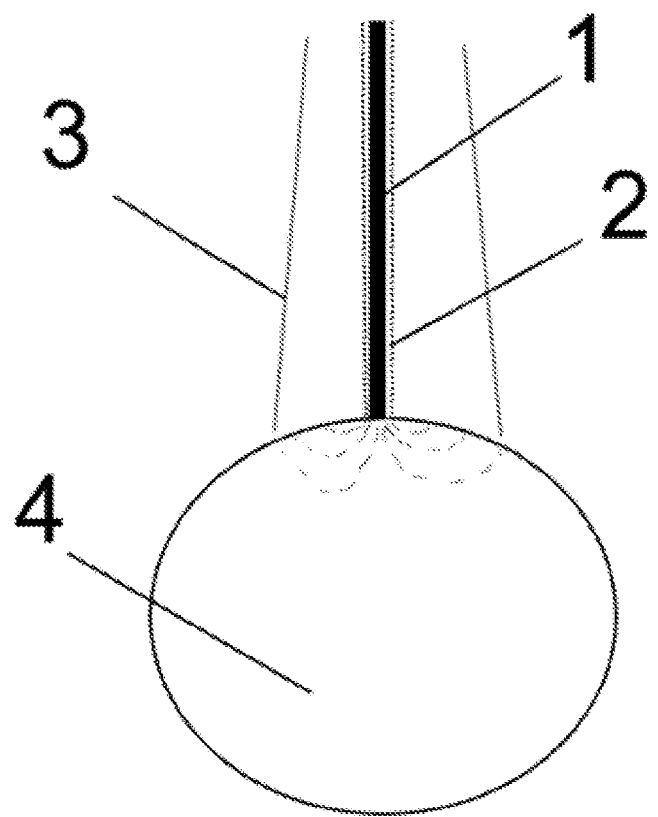
FIG. 2 shows the spot light beam striking the product as described in the present invention.

FIG. 2 depicts the spot light beam (1) striking the product (4) where it can be seen that the beam is of a small size and produces a reflected beam (2) and a halo (3) around the actual beam generated based on the light that has penetrated the product and then internally scattered. So, when the light of the mentioned halo is analyzed, analysis is being performed on the light of the spot beam which has partially gone through the product (4) and scattered inside the same.

Figure 3:
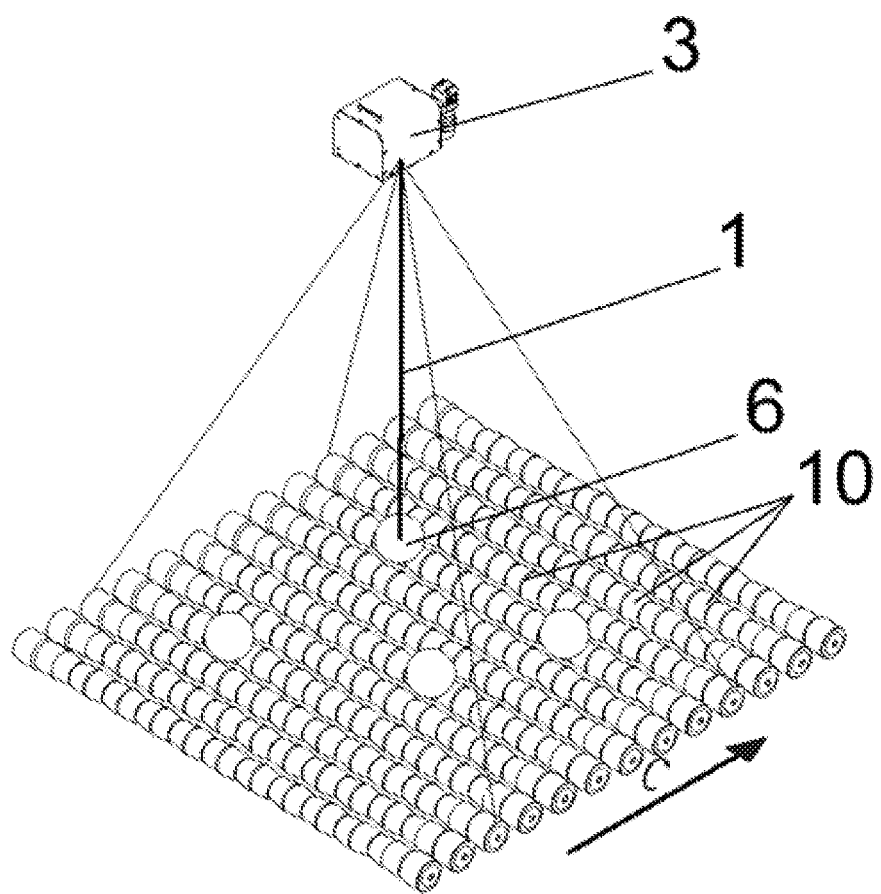
FIG. 3 shows the device according to the invention being used with a rotating roller conveyance system.

Another preferred way of assembling the system is in combination with a rotating roller conveyance system as depicted in FIG. 3. In this advantageous combination, readings of the different faces of the objects (6) can be taken as the objects are moved through the inspection region, rotating on their selves, by means of the rotating rollers (10). In this case, a two-axis galvanometer head (3) must be used to enable moving the inspection beam (1) both in the transverse direction with respect to the conveyance system, and in forward movement direction to analyze the same object at different instants of time (different faces can be analyzed given the rotation of the object). In this embodiment, certain positions of the product on the rollers can also be scanned continuously without having to previously determine whether or not the product is in said position. This is of particular interest if the roller conveyance system has rollers that position the product.

In another preferred embodiment, an element blocking the central part of the reflected beam will be installed in the optical system of at least one of the detectors. In this manner, light which has been reflected in a localized manner is eliminated from the return beam and only that light that has been scattered inside the product, i.e., which has interacted therewith, is analyzed.

This system, in combination with a spectrometer-type detector, preferably NIR, allows obtaining chemical information about the product.

In another preferred embodiment, an area detector will be used for analyzing the size and the form of scattering of the beam in the product to be inspected.

In another preferred embodiment, a filter for eliminating certain wavelengths will be installed in the light beam, at the outlet of the source. This makes the detection of the fluorescence easier because it is will be easier to detect this faint signal if the wavelengths where fluorescence occurs are eliminated from the light source.

In another preferred embodiment, several fast point detectors (for example, solid-state photomultiplier tubes) will be used in combination with several mirrors reflecting certain wavelengths of interest. The fast measurement based on certain spectral ranges of interest is therefore made possible.

The invention claimed is:

1. A product inspection and characterization device, comprising:
product conveyance means in the form of a conveyor belt or roller conveyor, the product conveying means being configured for continuous movement of products,
a two-dimensional inspection region through which the products are moved by the conveyance means,
a radiation source generating a spot light beam to at least partially illuminate a surface of the product,
an optical means configured for directing the light beam to the inspection region, which are provided with two mirrors assembled on two perpendicular axes consisting of an X axis and a Y axis,
wherein one mirror moves in the X axis and the other mirror moves in the Y axis,
detection means for analyzing the light scattered and/or reflected by the product,
further optical means for directing the reflected and/or scattered light to the detection means,
a processor for characterizing the product,
wherein the radiation source emits a spot light beam that is pointed at the product by the optical means which are configured for directing the light beam to the two-dimensional inspection region.

2. The inspection and characterization device according to claim 1, wherein the conveyance means comprise a roller conveyor, such that the product rotates about itself while at the same time moves forward through the inspection region, so that each product can be inspected on different sides.

3. The inspection and characterization device according to claim 1, wherein the device comprises a vision system for detecting a position of the objects to be inspected and directing the light beam thereon.

4. The inspection and characterization device according to claim 1, wherein the optical means comprise a blocking element to prevent the reflected light from returning to the detection means.

5. The inspection and characterization device according to claim 1, wherein the further optical means comprise means for independently collecting the reflected light and the scattered light to send it to different detection means.

6. The inspection and characterization device according to claim 1, wherein the detection means for analyzing the scattered light comprise at least one spectrometer.

7. The inspection and characterization device according to claim 1, wherein the radiation source is a supercontinuum laser.

8. The inspection and characterization device according to claim 1, wherein the optical means for directing the reflected and/or scattered light comprise light beam splitting elements and filters.

9. The inspection and characterization device according to claim 1, including means for sorting the product.

10. A method for product inspection and characterization which comprises the following steps:
moving the product through the detection region with a conveyance means,
emitting a light beam by a radiation source,
orienting the path of the light beam by means of moving two mirrors assembled on two perpendicular axes consisting of an X axis and a Y axis so that one mirror moves on the X axis and one mirror moves on the Y-axis to direct the light beam on the products to be inspected,
projecting the emitted spot light beam on the product,
returning the emitted light which has been reflected and/or scattered by the product,
measuring the reflected and/or scattered light,
analyzing the measurement to obtain a characterization of the product, and
sorting the product based on the obtained characterization.

11. The method for inspection and characterization according to claim 10, wherein the method incorporates a step of detecting a position of the product to be inspected by means of the vision system.

12. The method for inspection and characterization according to claim 10, wherein after the return of the emitted light, a step of filtering certain wavelengths of the reflected and/or scattered light beam is performed.

13. The method for inspection and characterization according to claim 10, wherein the measurement of the reflected and/or scattered light is a spectral measurement performed by detection means provided with a spectrometer.

14. The method for inspection and characterization according to claim 10, wherein as the product moves through the inspection region, the product rotates on itself, so that the same product is inspected on different sides at different instants of time.

* * * * *